US010486967B2

(12) United States Patent
Isobe et al.

(10) Patent No.: US 10,486,967 B2
(45) Date of Patent: Nov. 26, 2019

(54) INDUCTIVELY HEATED METHANE PYROLYSIS REACTOR FOR ADVANCED OXYGEN RECOVERY IN ENVIRONMENTAL CONTROL AND LIFE SUPPORT SYSTEMS

(71) Applicant: HONEYWELL INTERNATIONAL INC., Morris Plains, NJ (US)

(72) Inventors: Jun Isobe, Torrance, CA (US); Charles Lo, Peoria, AZ (US); Amanda Childers, Des Plaines, IL (US); Stephen Yates, South Barrington, IL (US); Dale Winton, Mission Viejo, CA (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 282 days.

(21) Appl. No.: 15/586,590

(22) Filed: May 4, 2017

(65) Prior Publication Data

US 2018/0319661 A1 Nov. 8, 2018

(51) Int. Cl.
*C01B 3/24* (2006.01)
*C07C 1/12* (2006.01)
*C25B 1/04* (2006.01)

(52) U.S. Cl.
CPC .............. *C01B 3/24* (2013.01); *C07C 1/12* (2013.01); *C25B 1/04* (2013.01); *C01B 2203/062* (2013.01); *C01B 2203/1241* (2013.01)

(58) Field of Classification Search
CPC ...................................................... C01B 3/24
See application file for complete search history.

(56) References Cited

U.S. PATENT DOCUMENTS

| 2,471,398 A | 5/1949 | Simpson et al. |
| 2,555,210 A | 5/1951 | Waddill et al. |
| 2,647,041 A | 7/1953 | Robinson |
| 2,656,306 A | 10/1953 | Bergstrom et al. |
| 3,079,237 A | 2/1963 | Taylor |
| 3,138,434 A | 6/1964 | Diefendorf |
| 3,340,012 A | 9/1967 | Moehl |
| 3,399,969 A | 9/1968 | Bokros et al. |
| 3,488,401 A | 1/1970 | Ames |
| 3,799,866 A | 3/1974 | Lengemann |
| 3,851,048 A | 11/1974 | Araki et al. |
| 3,907,948 A * | 9/1975 | Gyarmati ............... G21C 3/044 264/0.5 |
| 4,410,504 A | 10/1983 | Galasso et al. |

(Continued)

OTHER PUBLICATIONS

Christian Junaedi et al., "Compact and Lightweight Sabatier Reactor for Carbon Dioxide Reduction", 41st International Conference on Environmental Systems, American Institute of Aeronautics and Astronautics, 2011.

(Continued)

*Primary Examiner* — Donald R Spamer
(74) *Attorney, Agent, or Firm* — Shimokaji IP

(57) ABSTRACT

A pyrolysis reactor includes a chamber having an inactive section and an active section. The inactive section is configured to hold an inactive pre-form capable of adhering carbon. The active section is configured to hold an active pre-form capable of adhering carbon. An induction coil is outside of and operatively adjacent the active section, and wherein the active section is configured to pyrolyze a hydrocarbon.

9 Claims, 6 Drawing Sheets

(56) References Cited

U.S. PATENT DOCUMENTS

| | | | |
|---|---|---|---|
| 4,452,676 A | | 6/1984 | Birbara et al. |
| 4,770,867 A | | 9/1988 | Le Carbone-Lorraine |
| 5,061,455 A | | 10/1991 | Brose et al. |
| 5,362,373 A | | 11/1994 | Murdoch et al. |
| 5,418,063 A | * | 5/1995 | Booth .................... C04B 35/83 427/113 |
| 5,981,827 A | * | 11/1999 | Devlin .................... C04B 41/85 623/23.51 |
| 6,221,475 B1 | | 4/2001 | Domergue et al. |
| 8,945,351 B2 | | 2/2015 | Bratina et al. |
| 2004/0112741 A1 | | 6/2004 | Murdoch |
| 2004/0149209 A1 | * | 8/2004 | Dai .................... B82Y 30/00 118/715 |
| 2009/0317642 A1 | * | 12/2009 | Goller .................... C04B 35/565 428/450 |
| 2012/0066974 A1 | * | 3/2012 | Jorgenson .................... C10B 1/10 48/61 |
| 2012/0259025 A1 | | 10/2012 | Zhao |
| 2012/0321779 A1 | * | 12/2012 | Vargas .................... C23C 16/045 427/2.26 |
| 2015/0010452 A1 | | 1/2015 | Elliott et al. |
| 2015/0147259 A1 | | 5/2015 | Noyes |
| 2016/0016794 A1 | | 1/2016 | Noyes |
| 2016/0017800 A1 | | 1/2016 | Simpson |
| 2016/0083658 A1 | | 3/2016 | Sanner |
| 2016/0230311 A1 | | 8/2016 | Vince |
| 2017/0239609 A1 | * | 8/2017 | Luisman ............ B01D 53/0423 |

OTHER PUBLICATIONS

P. K. Sharma et al., "Methane Pyrolysis and Disposing Off Resulting Carbon", In Situ Resource Utilization (ISRU 3) Technical Interchange Meeting: Abstracts; 31-32, 1999.

Robert J. Erickson et al., "International Space Station United States Orbital Segment Oxygen Generation System On-orbit Operational Experience," SAE Int. J. Aerosp. 1(1):15-24, 2009.

Kevin C. Takada et al., "Advancing the Oxygen Generation Assembly Design to Increase Reliability and Reduce Costs for a Future Long Duration Mission", 45th International Conference on Environmental Systems, Texas Tech University, 2015.

* cited by examiner

INDUCTIVELY HEATED METHANE PYROLYSIS REACTOR FOR ADVANCED OXYGEN RECOVERY IN ENVIRONMENTAL CONTROL AND LIFE SUPPORT SYSTEMS

BACKGROUND OF THE INVENTION

The present invention generally relates to oxygen recovery and, more particularly, to apparatus and methods of oxygen recovery in closed environments.

In long duration manned missions to Mars, the Moon, asteroids, etc. carrying sufficient oxygen to provide for the needs of the crew is a critical obstacle. NASA believes that the only solution is a "closed loop" in which the carbon dioxide exhaled by crew members is chemically converted back to oxygen. This has been a NASA goal for a number of years, but an effective solution to the problem has not been discovered.

Current processes that are well known to those skilled in the art, and which are in use on the International Space Station (ISS) include the Carbon Dioxide Removal Assembly (CDRA) which recovers carbon dioxide from the atmosphere in the cabin, and the Oxygen Generation Assembly (OGA) which uses electrolysis of water to generate hydrogen and oxygen. A developmental Sabatier reactor is in evaluation on the ISS which uses the hydrogen from the OGA to reduce the carbon dioxide from the CDRA to methane and water. The water can then be sent to the OGA to make oxygen.

However, only 50% of the CO2 can be reduced, because the Sabatier reaction requires 4 moles of hydrogen, while the OGA reaction only generates 2 moles. This limits oxygen recovery to <50%. The hydrogen "wasted" in making methane must be recovered. Methane pyrolysis can be of limited use. Others have tried to accomplish methane pyrolysis using microwaves, among other techniques, but they generate mostly acetylene, rather than carbon, so the maximum possible hydrogen recovery is reduced.

Acetylene is both flammable and explosive. Generation of this gas requires that it be promptly vented for safety reasons. The quantities generated by these other technologies are significant, meaning that a significant gap in loop closure will be involved. Some prior processes generate carbon via either the Bosch or Boudouard reactions. However, because these reactions are catalytic, and the carbon accumulates on and fouls the catalyst, they must be cleaned periodically, generating carbon dust. Other processes directly generate carbon soot.

Dust and soot are particularly difficult to deal with in a zero gravity environment since they can foul or escape from filters, and because they represent both an inhalation hazard to people and a threat to equipment. Uncontrolled soot generation can clog reactors and tubes. Even if soot or dust is vented from the spacecraft, it can be damaging. Soot in the vicinity of the spacecraft may coat solar panels or other exterior structures. In a Mars habitat scenario, discharging soot may contaminate the environment near the habitat, interfering with experimentation or affecting the operation of other equipment.

As can be seen, there is a need for improved apparatus and methods to recover oxygen in closed and/or gravity-free environments such as deep space vehicles.

SUMMARY OF THE INVENTION

In one aspect of the present invention, an environmental control system comprises an environmental control system comprises a carbon dioxide source; a compressor downstream of the carbon dioxide source; a Sabatier reactor downstream of the compressor, wherein the Sabatier reactor produces methane and water; a water separator downstream of the Sabatier reactor, wherein the water separator produces methane and water; a pyrolysis reactor downstream of the water separator and upstream of the compressor, wherein the pyrolysis reactor includes: a chamber configured to concurrently hold a plurality of pre-forms; wherein the pre-forms are configured to move along a longitudinal length of the chamber; wherein the pre-forms are configured to adhere carbon; wherein the pyrolysis reactor produces hydrogen; and an oxygen generating assembly (OGA) downstream of the water separator and upstream of the compressor, wherein the OGA produces hydrogen and oxygen.

In another aspect of the present invention, a pyrolysis reactor comprises a chamber having an inactive section and an active section; wherein the inactive section is configured to hold an inactive pre-form capable of adhering carbon; wherein the active section is configured to hold an active pre-form capable of adhering carbon; an induction coil that is outside of and operatively adjacent to the active section; and wherein the active section is configured to pyrolyze a hydrocarbon.

In a further aspect of the present invention, a pyrolysis reactor comprises a chamber configured to concurrently hold a plurality of pre-forms in an end-to-end relationship; an induction coil that circumferentially surrounds the chamber; an advancer that moves the plurality of pre-forms along a longitudinal length of the chamber; wherein, at any given time, one to a plurality of pre-forms are operatively adjacent the induction coil; a methane inlet into the chamber; and a hydrogen outlet out of the chamber.

These and other features, aspects and advantages of the present invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

Broadly, the present invention can be integrated into environments such as spacecraft used in long-duration missions, specifically, space stations and spacecraft and habitats used in and beyond low earth orbit, as the invention can operate independent of gravity. The present invention may also be used for aircraft, as another example, where its gravity independence would help mitigate failures due to managing liquids under turbulence.

The present invention may be an environmental control system, such as an Environmental Control and Life Support System (ECLSS). A methane pyrolysis reactor can be combined with a Sabatier reactor and an Oxygen Generating System (OGA) in such a way that the net result is more than the sum of the parts. The reduction of carbon dioxide to recover oxygen requires hydrogen, which can be provided by the OGA. The OGA may not provide enough hydrogen to reduce all of the $CO_2$, given the Sabatier chemical reaction, which produces methane and water. As a result, oxygen can only be recovered from half the $CO_2$. However, the present invention can recover hydrogen from the produced methane via pyrolysis, restoring the required balance between carbon dioxide and hydrogen. By restoring this balance, the theoretical oxygen recovery, based on stoichiometry, is 100%:

Sabatier:

$$CO_2 + 4H_2 \longrightarrow CH_4 + 2H_2O$$

Electrolysis:

$$2H_2O \longrightarrow 2H_2 + O_2$$

Pyrolysis:

$$CH_4 \xrightarrow{\Delta} 2H_2 + C$$

Net reaction:

$$CO_2 + O_2 + C$$

An environmental control system employing a Sabatier reactor, OGA, and pyrolysis reactor are described in US patent application entitled "Integrated System for Oxygen Recovery for Deep Space Mission, concurrently filed herewith and incorporated herein in its entirety.

In the pyrolysis reactor, a disposable pre-form insert can have a high surface area on which carbon can grow by carbon vapor deposition/infiltration. The presence of this high surface area changes the product distribution to make more carbon and hydrogen, and less of other gas phase hydrocarbons.

Figure 1:
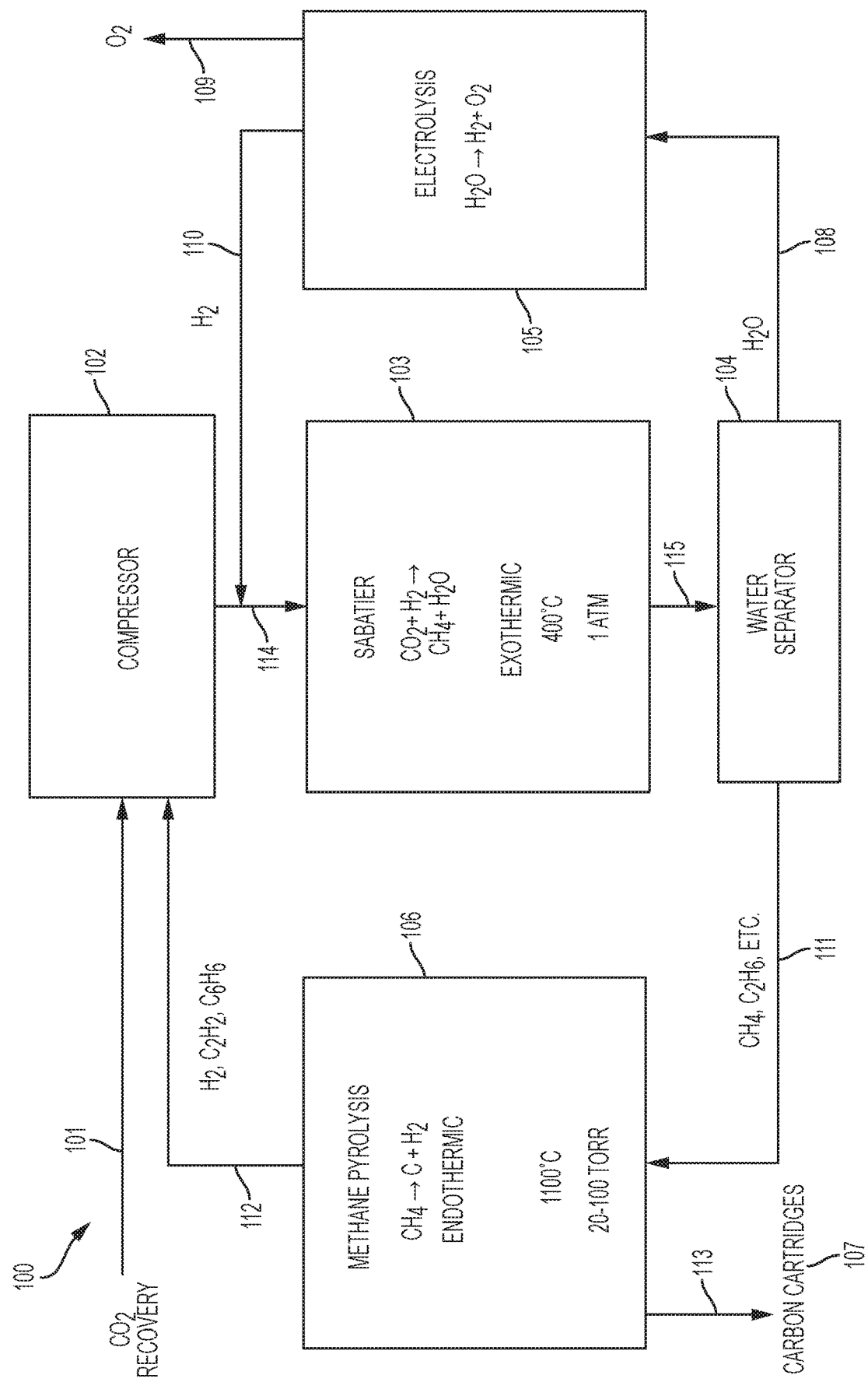
FIG. 1 is a schematic diagram of an environmental control system (ECS) in accordance with an exemplary embodiment of the present invention.

FIG. 1 is a schematic diagram of an exemplary embodiment of an environmental control system (ECS) 100, such as an Environmental Control and Life Support System (ECLSS). The ECS 100 may receive $CO_2$ from a carbon dioxide source 101, for example, a Carbon Dioxide Removal Assembly (CDRA). A compressor 102, downstream of the $CO_2$ source 101, may receive the $CO_2$ from the carbon dioxide source 101. After compression it may be mixed with hydrogen from an Oxygen Generating Assembly (OGA) 105, further described below. This mixture 114 will thus comprise a mixture of $CO_2$ and $H_2$.

In embodiments, the compressed mixture 114 of $CO_2$ and $H_2$ may be at a pressure of about 1 atm. In embodiments, the compressed mixture may be in a mole ratio of about 4 to about 5, $H_2$ to $CO_2$.

A reactor 103, such as a Sabatier reactor, downstream of the compressor 102, may receive and cause the compressed mixture 114 to undergo the following reaction:

Sabatier: $CO_2 + 4H_2 \rightarrow CH_4 + 2H_2O$

Sabatier reactors are well known in the art and described, for example, in Junaedi et al., "Compact and Lightweight Sabatier Reactor for Carbon Dioxide Reduction", $41^{st}$ International Conference on Environmental Systems, 2011, American Institute of Aeronautics and Astronautics, https://ntrs.nasa.gov/archive/nasa/casi.ntrs.nasa.gov/20120016419.pdf, which is incorporated herein in its entirety. The Sabatier reactor 103 may be of conventional design and, in embodiments, operate at about 400° C. and 1 atm in the presence of a catalyst such as nickel or ruthenium. The reaction is exothermic. Thus, heat must be supplied at start up, but after that point, it should instead be cooled. Products 115 exiting the Sabatier reactor 103 include methane and water.

A water extractor 104, downstream of the Sabatier reactor 103, may be in the form of a condenser, in some embodiments. In other embodiments, the water extractor 104 may have a zeolite membrane. Accordingly, the water extractor 104 may produce water 108 separated hydrocarbons 111. The hydrocarbons 111 may include methane and ethane —$CH_4$ and $C_2H_6$. In embodiments, the methane may be present at greater than about 90% of the hydrocarbons 111.

A pyrolysis reactor 106, downstream of the water separator 104, may receive the hydrocarbons 111. In embodiments, a concentration of water entering the pyrolysis assembly 106 is kept low—such as less than about 1%—since, in the presence of water, the thermodynamically preferred product is CO, not carbon.

The pyrolysis reactor 106 may, in embodiments, operate at about 1100°-1200° C., and about 20-100 torr. Thus, the pyrolysis assembly 106 may cause methane to be pyrolyzed according to the following reaction:

Pyrolysis:

$$CH_4 \xrightarrow{\Delta} 2H_2 + C$$

Also produced by the pyrolysis reactor 106 may be hydrocarbons such as acetylene and benzene —$C_2H_2$ and $C_6H_6$. In embodiments, the pyrolysis assembly 106 may consume about 1.51 kg/day of methane and produce about 0.38 kg/day of hydrogen at a 100% yield.

Figure 2A:
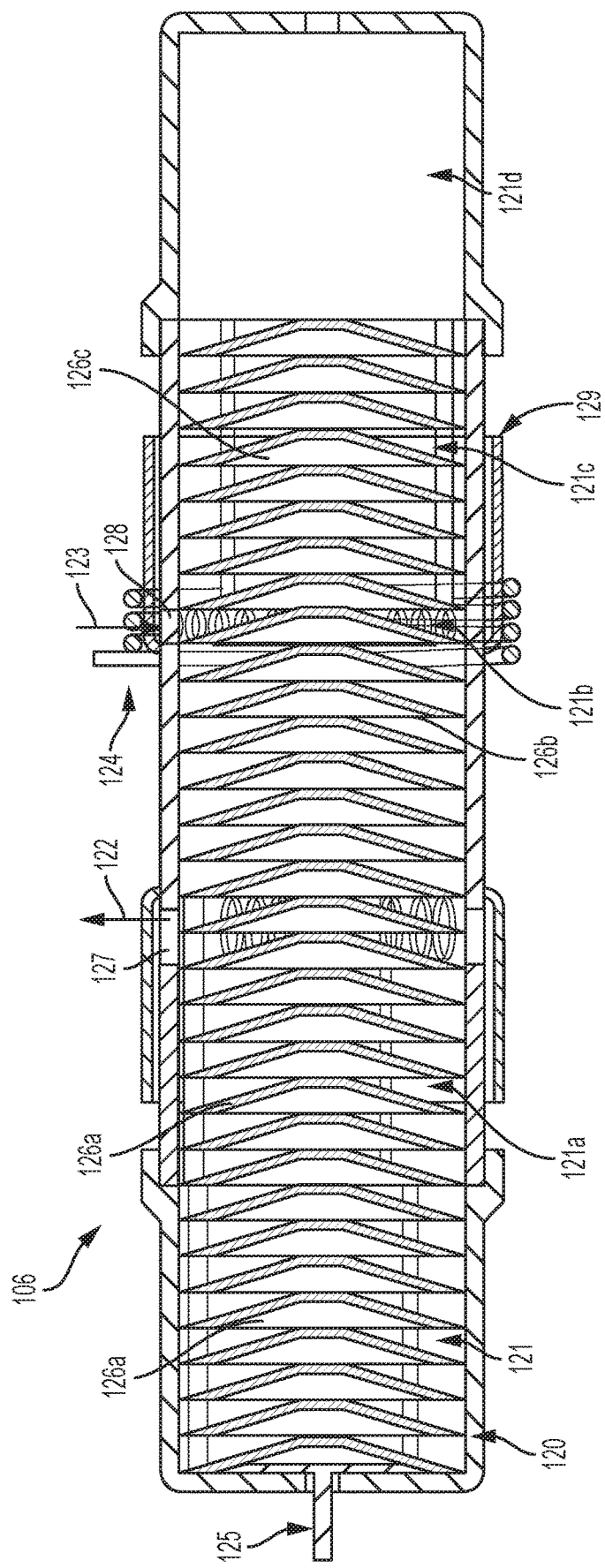
FIG. 2A is a cross-sectional view of a pyrolysis reactor of an ECS in accordance with an exemplary embodiment of the present invention.

In FIG. 2A, the pyrolysis reactor 106 may include a housing 120 made of a material such as ceramic or quart. The housing 120 may form a chamber 121 along a longitudinal length or axis. The chamber 121 may include chamber portions 121*a-d* that are positioned along the longitudinal length of the chamber 121.

In some embodiments, the chamber portion 121*a* may be a portion of the chamber 121 wherein a produced gas, such as $H_2$, collects and exits the chamber, as further described below. In some embodiments, the chamber portion 121*b* may be a portion of the chamber 121 wherein a reactant hydrocarbon, such as $CH_4$, may enter the chamber. The chamber portion 121b may also be where the hydrocarbon is pyrolyzed, such as $CH_4$ being pyrolyzed to $H_2$ and C. The chamber portion 121c, for example, may be a portion of the chamber 121 where a carbon-loaded pre-form may temporarily reside, as further described below. In embodiments, the chamber portion 121d may be a portion of the chamber 121 where a carbon-loaded pre-form may be stored.

One or more of the chamber portions 121a-d may form an active section and an inactive section of the chamber 121, according to embodiments. In certain embodiments, the active section may only include the chamber portion 121b. In other embodiments, the inactive section may include one or more of the chamber portions 121a, c, d, but not the chamber portion 121b.

According to embodiments, the active section of the chamber 121 may be configured to hold only one active pre-form (although more than one pre-form is envisioned), as further described below. And the inactive section of the chamber 121 may be configured to hold one or more inactive pre-forms, as further described below.

Figure 4A:
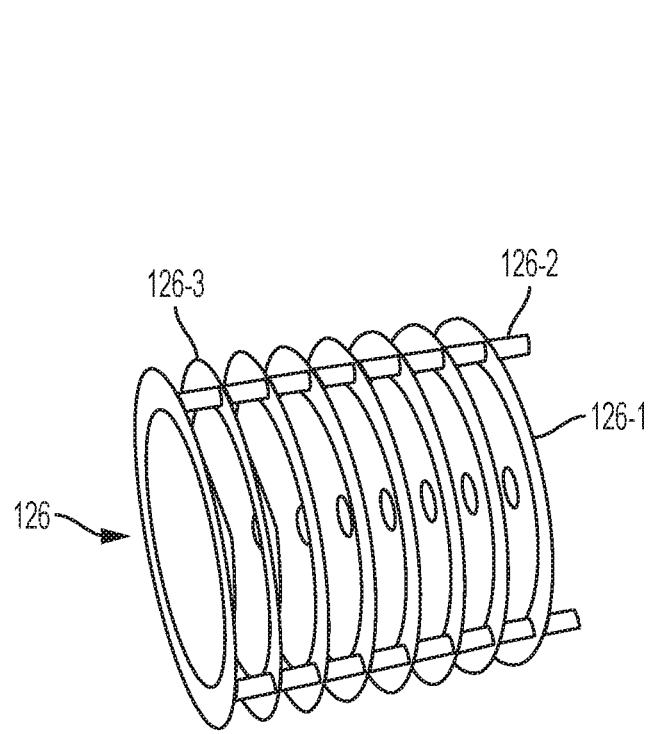
FIGS. 4A-C are views of a pre-form and its components of a pyrolysis reactor in accordance with an exemplary embodiment of the present invention.
Figure 4B:
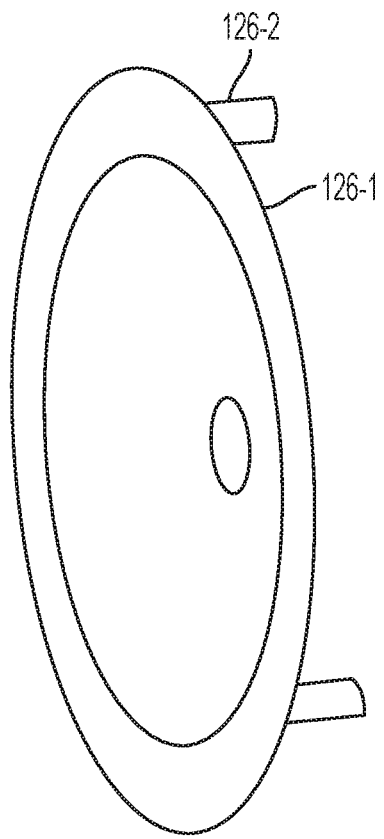
Figure 4C:
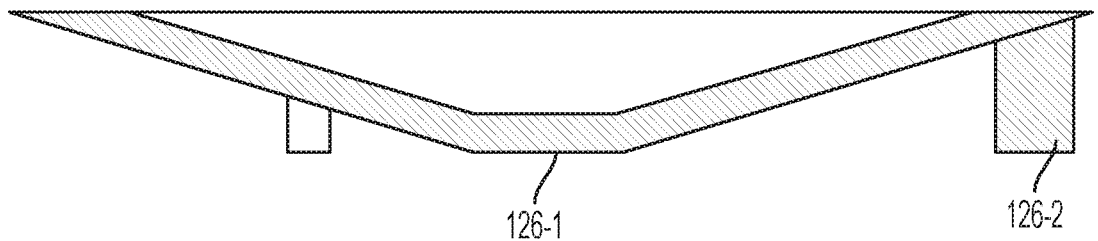

In FIG. 2A, a plurality of pre-forms 126a, b, c, with two pre-forms 126a being present. According to certain embodiments, as shown in FIGS. 4A-C, one or more of the pre-forms 126 may be in the form of a disc, and a plurality of pre-forms may form a cartridge. Thus, a cartridge may include a plurality of stacked discs or pre-forms 126-1. One or more of the discs 126-1 may be made of loosely packed carbon fibers. Alternatively, the carbon fiber discs may contain a high-surface-area ferromagnetic core to act as a susceptor for additional heating. And one or more pairs of immediately adjacent discs 126-1 are separated by an air-gap 126-3.

In the embodiments of FIGS. 4A-C, the discs 126-1 can be held together by a scaffold 126-2 made of legs attached to the discs 126-1. The scaffold 126-2 can be made of the same material as the pre-form.

Referring back to FIG. 2A, a reactant inlet 128 into the chamber 121 may be operatively adjacent the active section, such as the chamber portion 121b as an example. The inlet 128 can enable a pre-heated hydrocarbon (e.g., $CH_4$) 123 to enter, via a manifold 129, the active section of the chamber 121. A produced gas outlet 127 out of the chamber 121 may be operatively adjacent the inactive section, such as the chamber portion 121a. The outlet 127 can enable a produced gas (e.g., $H_2$) 122, resulting from pyrolysis of the pre-heated hydrocarbon, to exit the inactive section of the chamber 121.

To enable pyrolysis, an induction coil 124 may circumferentially surround an exterior of the chamber 121. In embodiments, the coil 124 may only surround the active section of the chamber 121, such as the chamber portion 121b. As an example, the coil 124 may have about 2 to about 6 turns.

If the induction coil 124 only surrounds the active section of the chamber 121, and there is only one pre-form 126 in the active section, that one pre-form 126 may be considered as an active pre-form. This is because, upon an alternating current passing through the coil 124, the coil 124 can generate heat, inductively, in essentially only the one pre-form 126 that is disposed in the active section. Thus, as an example in FIG. 2A, only the pre-form 126b is in the active section and is inductively heated by the coil 124. At the same time, the pre-forms 126a, c are in the inactive section and essentially remain unheated by the coil 124. In embodiments, the pre-forms 126c may be cooled and/or cooling down after heating.

In embodiments, an advancer element 125 that has a piston or plunger-like configuration that can be actuated to move the plurality of pre-forms 126, in an end-to-end relationship, along the longitudinal length of the chamber 121. Accordingly, for example, a pre-form 126 can be moved from one end of the chamber 121 towards an opposite end of the chamber 121. Thereby, a pre-form can start in the inactive section where pre-form is inactive, move into active section where the pre-form becomes active, and then move back into the inactive section where the pre-form is once again inactive.

As noted above, inductive heating of the pre-form 126 is employed. This can focus the heat on the pre-form itself, rather than heating from the outside edges as would be the case with resistive/radiative heating. The pre-form 126 can be composed of a high surface area material, such as a loosely woven or unwoven fabric or highly porous solid. An architecture could prevent clogging of the porous pathways (e.g., by using larger pores near the surface of the pre-form). To be heated by induction heating, the pre-form can be made of a magnetically susceptible material, or it can include a magnetically susceptible material inserted within the pre-form to act as a susceptor and promote heating indirectly.

Examples of a pre-form composed of a magnetically susceptible material include layers of carbon fiber mats/fabrics or steel wool. Examples of an added susceptor design include a thin metal mesh at the center plane of the preform or a porous metal rod inserted along the center axis of the preform.

In embodiments, the pre-form is fabricated from loosely packed carbon fibers, about 5% to 20% fiber volume, that loops around the axis to form a disc; in another embodiment, the carbon fiber discs surround the both sides of a thin ferrous-meshed disc susceptor for additional heat gain from magnetic hysteresis. Induction heating also has the capability to produce a lighter, more power efficient unit as compared to other heating methods. Because only the pre-form 126 is heated, it can be heated rapidly to the required temperature. This can minimize "down time" after change out of pre-forms, as described below. By reducing the size of the heated zone, it also reduces power consumption and heat losses.

The pre-form functions by providing a surface onto which carbon vapor deposition can occur. The greater the surface area/volume ratio, the more surface the pre-form will have. A pre-form with higher surface area/volume will accumulate carbon more rapidly, and therefore generate a higher hydrogen yield. In an embodiment, the pre-form may comprise numerous small fibers. It is desirable that the surface area/volume for the pre-form be at least 20 $cm^{-1}$.

The use of pre-forms is also described in US patent application entitled "Integrated System for Oxygen Recovery for Deep Space Mission, concurrently filed herewith and incorporated herein in its entirety.

Figure 2B:
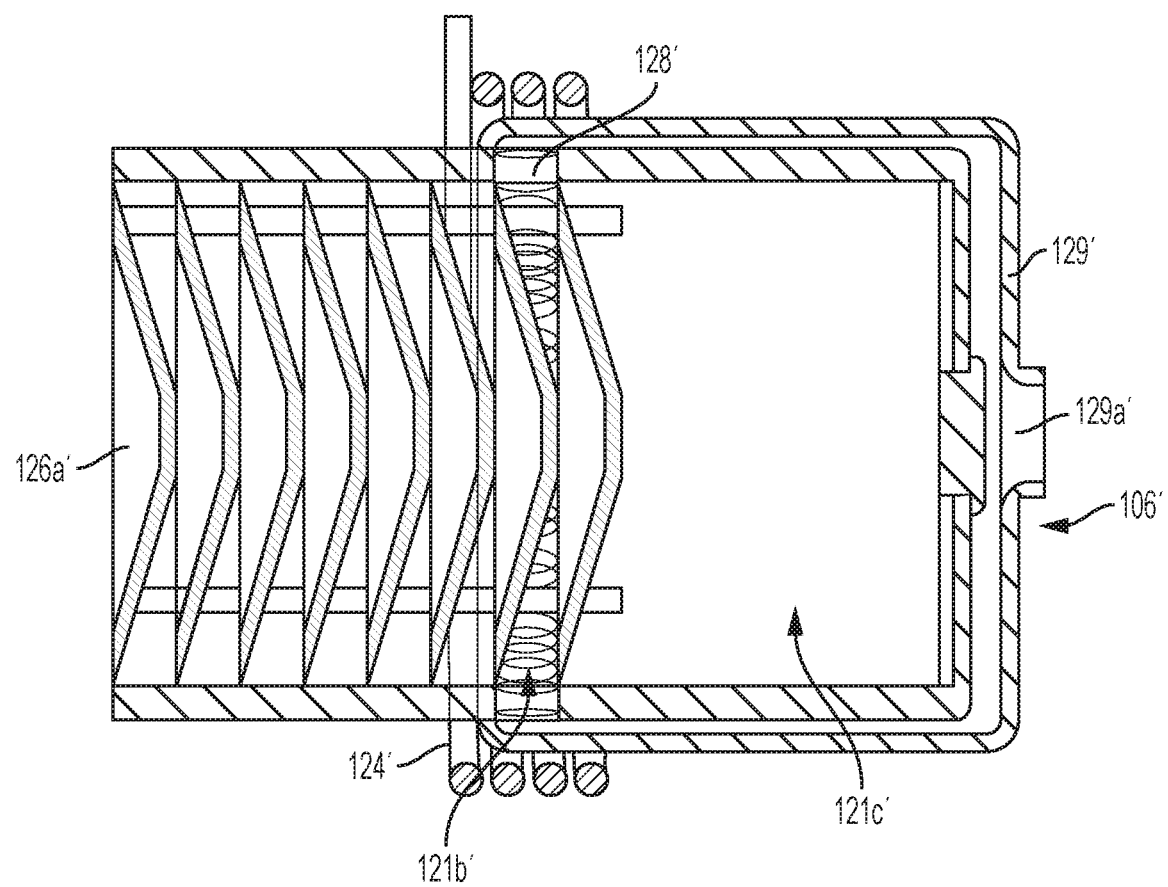
FIG. 2B. is a partial cross-sectional view of a pyrolysis reactor of an ECS in accordance with another exemplary embodiment of the present invention.

FIG. 2B is a partial view another embodiment a pyrolysis reactor 106'. The reactor 106' is similar to the reactor 106 of FIG. 2A. However, in the former, a manifold 129' enables a pre-heated hydrocarbon to enter an inlet 129a' which is located centrally of the chamber 121. Accordingly, there is an absence of a pre-form storage portion in the reactor 106'. In the reactor 106, a pre-heated hydrocarbon enters the manifold 129 circumferentially about the chamber 121 and includes a storage portion 121d.

Figure 3:
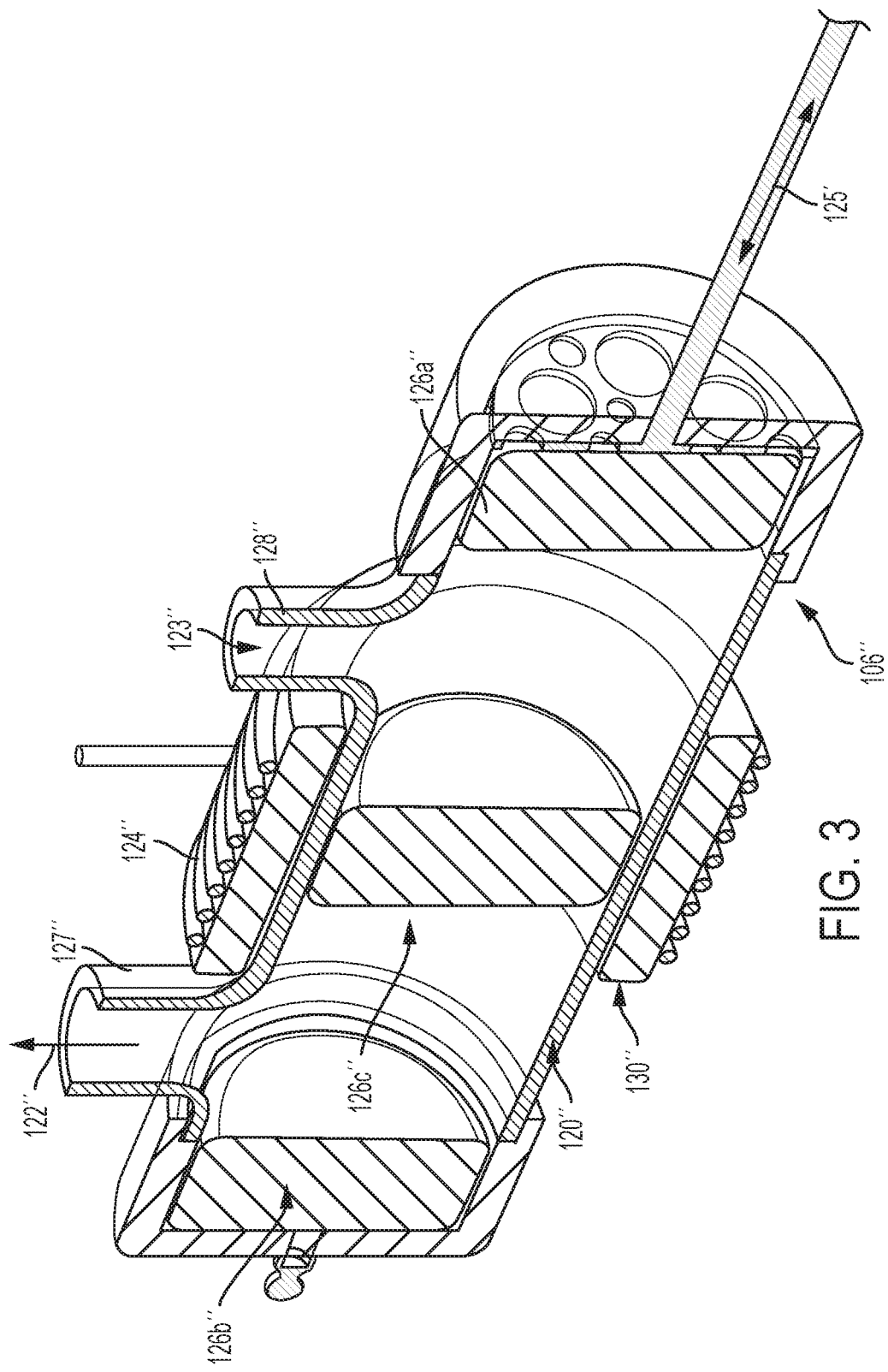
FIG. 3. is an exploded, cross-sectional, perspective view of a pyrolysis reactor of an ECS in accordance with yet a further exemplary embodiment of the present invention.

FIG. 3 is a view of yet a further embodiment of a pyrolysis reactor 106". This embodiment is similar to the reactor 106 of FIG. 2A. However, in the former, an insulation layer 130" is disposed between the induction coil 124" and the housing 120". Also, in the former, the coil 124" has more windings than the coil 124, and the pre-forms 126a", b", c" are solid configurations rather than stacked discs.

Figure 5:
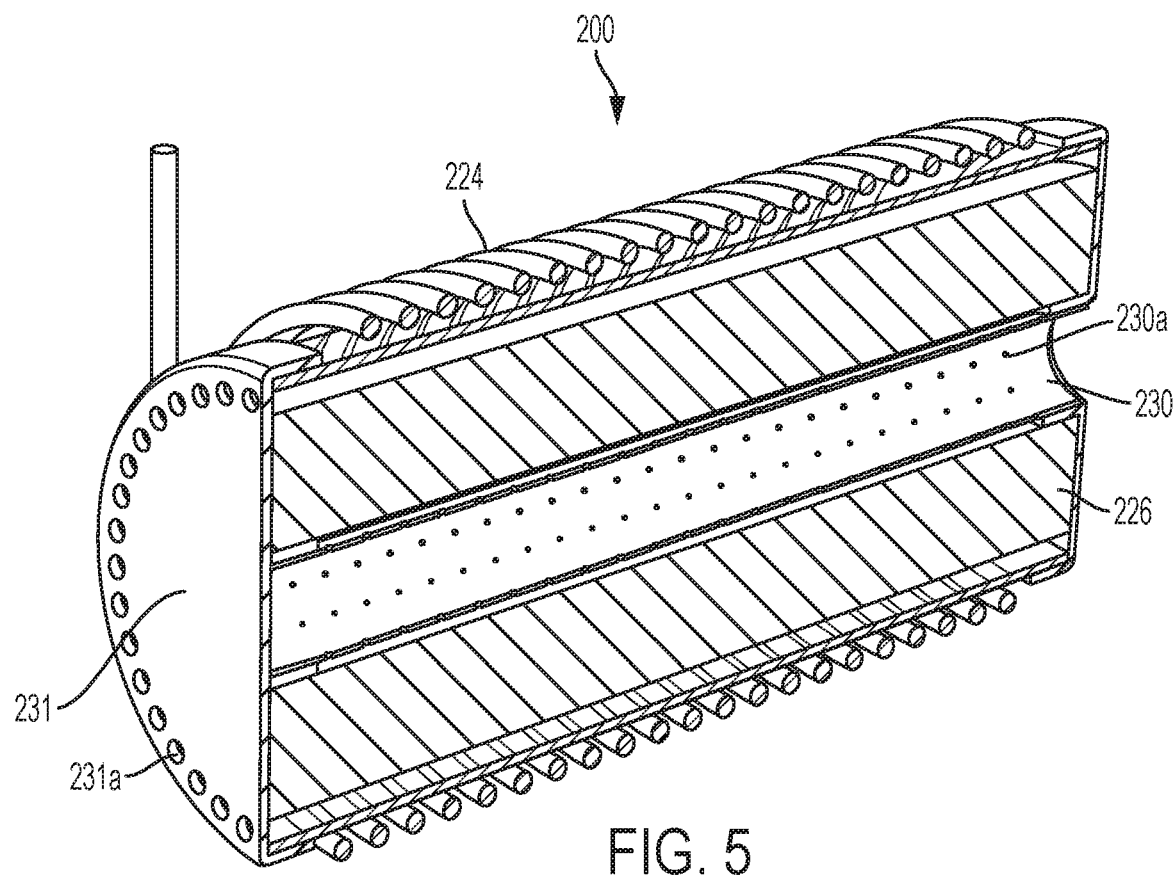
FIG. 5 is a cross-sectional, perspective view of a pyrolysis reactor of an ECS in accordance with yet another exemplary embodiment of the present invention.

FIG. 5 is yet another embodiment of a pyrolysis reactor 200 which is similar to the reactor 106 of FIG. 2A. However, in the reactor 200, the reactant hydrocarbon (e.g., CH$_4$) enters a longitudinal extending manifold 230 having outlet holes 230a. The manifold 230 is pipe-shaped and extends within and along a longitudinal axis of a pre-form 226. In an embodiment, the pre-form 226 is of a solid configuration, rather than a plurality of discs as in FIG. 2A. Nevertheless, the present invention contemplates that the pre-form 226 can be a plurality of discs.

Accordingly, methane can radially exit the manifold 230, via the holes 230a, to contact the pre-form 226. An induction coil 224 can be controlled at different frequencies to create a temperature gradient in the pre-form 226. In turn, the temperature gradient can alter the performance of the reactor 200, i.e., where pyrolysis occurs, radially, relative to the pre-form 226. Produced gas (e.g., H$_2$) may then exit the reactor 200, via an outlet manifold 231 and its outlet holes 231a.

Referring back to FIG. 1, pyrolysis products 112 may exit the pyrolysis reactor 106 and enter the compressor 102. The pyrolysis products 112 may include H$_2$, C$_2$H$_2$ and C$_6$H$_6$. In embodiments, H$_2$ may be present in the pyrolysis products from about 50 to about 90 volume percent.

The Oxygen Generating Assembly (OGA) 105 is upstream of the compressor 102 and downstream of the water separator 108. Accordingly, the OGA 105 may receive H$_2$O 108 from the water separator 108. In the OGA 105, H$_2$O may undergo electrolysis according to the following:

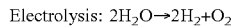

Electrolysis: 2H$_2$O→2H$_2$+O$_2$

The OGA 105 may be of conventional design and, in embodiments, operate at the conditions described, for example in Takada et. al., "Advancing the Oxygen Generation Assembly Design to Increase Reliability and Reduce Costs for a Future Long Duration Mission" 45th International Conference on Environmental Systems, July 2015; Erickson et. al., "International Space Station United States Orbital Segment Oxygen Generation System On-orbit Operational Experience" International Conference on Environmental Systems (ICES); 30 Jun.-3 Jul. 2008; San Francisco, Calif., SAE Int. J. Aerosp. 1(1):15-24, 2009, both of which are incorporated herein in their entirety. The produced O$_2$ 109 from the OGA 105 may be routed for use by occupants associated with the ECS 100. The produced H$_2$ 110 from the OGA 105 may be routed to the compressor 102.

Taking into account the H$_2$ from the OGA 105 and from the pyrolysis assembly 106, total H$_2$ to total CO$_2$ entering the compressor 102 may be in a molar ratio of about 4 to about 5.

In embodiments, the compressor 102 may maintain a partial vacuum in the pyrolysis reactor 106. Byproducts from the pyrolysis reactor 106—such as acetylene, ethylene and benzene—are delivered, along with the hydrogen, via the compressor 102 and to the Sabatier reactor 103. Under Sabatier conditions, these byproducts can be reduced to corresponding saturated alkanes, which become part of the feed to the pyrolysis reactor 106. Such alkanes can react to form carbon and hydrogen more rapidly than methane, so they can increase the output of carbon and hydrogen.

Viewed as a unit, the combination of the Sabatier reactor 103, the methane pyrolysis reactor 106, and the OGA 105 provide the following:

Net reaction: CO$_2$→O$_2$+C

In embodiments, methane pyrolysis can work well at temperatures >1100° C., and is endothermic. This can require about 450 W of power (assuming 1.5 kg/day methane flow). Since the Sabatier reactor 103 operates exothermically at 400° C., it can be used to pre-heat the methane for the pyrolysis assembly 106. This might be accomplished by completing the water recovery from the Sabatier reactor 103 at this temperature using a zeolite membrane, as noted above, or by inserting a heat exchanger to recover this heat.

It should be understood, of course, that the foregoing relates to exemplary embodiments of the invention and that modifications may be made without departing from the spirit and scope of the invention as set forth in the following claims.

We claim:
1. An environmental control system, comprising:
a carbon dioxide source that discharges a carbon dioxide flow;
a Sabatier reactor downstream, in terms of the carbon dioxide flow, of the carbon dioxide source, wherein the Sabatier reactor produces a product flow that contains methane and water;
a water separator downstream, in terms of the product flow, of the Sabatier reactor, wherein the water separator is directly connected to first ducting which is directly connected to the Sabatier reactor, wherein the first ducting conveys the product flow, wherein the water separator separates methane and water, wherein the water separator discharges a methane flow and a water flow;
a pyrolysis reactor downstream, in terms of the methane flow, of the water separator, wherein the pyrolysis reactor is directly connected to second ducting which is directly connected to the water separator, wherein the second ducting conveys the methane flow, wherein the pyrolysis reactor discharges a hydrogen flow, wherein the pyrolysis reactor is upstream, in terms of the hydrogen flow, of the Sabatier reactor, wherein the pyrolysis reactor includes:
 a chamber configured to concurrently hold a plurality of pre-forms;
 an induction coil that surrounds only an active section of the chamber;
 wherein the active section is configured to inductively heat a pre-form;
 a manifold that surrounds a housing of the chamber, and is between the housing and the induction coil;
 a hydrocarbon inlet in the housing, wherein the inlet is between the manifold and the chamber;
 wherein the pre-forms are configured to move along a longitudinal length of the chamber;
 wherein the pre-forms are configured to adhere carbon;
 wherein the pyrolysis reactor conveys the hydrogen flow directly to a compressor; and
an oxygen generating assembly (OGA) downstream, in terms of the water flow, of the water separator, wherein the OGA is directly connected to third ducting which is directly connected to the water separator, wherein the third ducting conveys the water flow, wherein the OGA produces hydrogen and oxygen, wherein the OGA is directly connected to fourth ducting which is directly connected to a carbon dioxide-hydrogen flow into the Sabatier reactor.
2. The system of claim 1, wherein the compressor is between the carbon dioxide source and the Sabatier reactor.

3. The system of claim 1, wherein the Sabatier reactor receives carbon dioxide from the carbon dioxide source and receives hydrogen from the OGA.

4. The system of claim 1, wherein the carbon dioxide source is a Carbon Dioxide Removal Assembly (CDRA).

5. The system of claim 1, wherein the system is in a gravity free environment.

6. The system of claim 1, wherein the system is in a deep space vehicle or on a planet.

7. A pyrolysis reactor, comprising:
   a chamber that holds a plurality of pre-forms;
   an induction coil that exteriorly surrounds only an active section of the chamber, wherein the induction coil has a longitudinal length parallel to a longitudinal axis of the chamber;
   wherein the active section is configured to inductively heat a pre-form;
   a manifold that surrounds a housing of the chamber, and is between the housing and the induction coil;
   a hydrocarbon inlet in the housing, wherein the inlet is only positioned within the longitudinal length of the induction coil;
   an advancer element that moves the plurality of pre-forms along a longitudinal length of the chamber; and
   a scaffold having legs that are attached to the plurality of pre-forms;
   wherein each of the plurality of pre-forms is in the form of a disc;
   wherein the plurality of pre-form discs are stacked in the form of a cartridge;
   wherein, at any given time, at least one pre-form can be operatively adjacent the induction coil; and
   a hydrogen outlet out of the chamber.

8. The reactor of claim 7, wherein the induction coil surrounds less than an entirety of the chamber.

9. The reactor of claim 7, wherein the pre-forms are electrically conductive and are heated by the induction coil.

* * * * *